US00PP28068P2

(12) United States Plant Patent
Van Swieten

(10) Patent No.: US PP28,068 P2
(45) Date of Patent: May 30, 2017

(54) *PHALAENOPSIS* ORCHID PLANT NAMED 'PHALCRYO'

(50) Latin Name: ***Phalaenopsis* hybrid**
Varietal Denomination: PHALCRYO

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 11 days.

(21) Appl. No.: 14/757,089

(22) Filed: Nov. 16, 2015

(51) Int. Cl.
*A01H 5/02* (2006.01)

(52) U.S. Cl.
USPC ..... Plt./311

(58) Field of Classification Search
USPC ..... Plt./311
See application file for complete search history.

(56) References Cited

PUBLICATIONS
UPOV—International Union for the Protection of New Varieties of Plants: PLUTO plant variety database, Jan. 17, 2017; citation for 'PHALCRYO' (1 pg total).*
Enclosure for the Plant Patent application of Anthura BV, 13 pages, 2015.
EU Community Plant Variety Rights Application No. 2014/2334, Application n°A201404656, filed Sep. 30, 2014, 7 pages.
EU Community Plant Variety Office Official Gazette, Jun. 2014, Dec. 15, 2014, cover page and pp. 36, 57.
EU Community Plant Variety Office Official Gazette, Mar. 2015, Jun. 15, 2015, cover page and p. 65.
EU Community Plant Variety Rights Application No. 2015/2493, Application n°A201502372, filed Oct. 30, 2015, 8 pages.
EU Community Plant Variety Office Official Gazette, Jun. 2015, Dec. 15, 2015, cover page and pp. 36, 55.
EU Community Plant Variety Office Official Gazette, Jan. 2017, Feb. 15, 2017, cover page and p. 70.

* cited by examiner

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALCRYO', particularly characterized by having small, light purple striped flowers with a light red-purple lip, 1 to 3 peduncles, an inflorescence that is short and moderate, leaves that are oblong, and is propagated by meristem tissue culture, is disclosed.

3 Drawing Sheets

Genus and species: *Phalaenopsis* hybrid.
Variety denomination: 'PHALCRYO'.

BACKGROUND OF THE NEW PLANT

The present invention comprises a new and distinct cultivar of *Phalaenopsis* plant, botanically known as *Phalaenopsis* of the Orchidaceae family, and hereinafter referred to by the cultivar name 'PHALCRYO'.

*Phalaenopsis* comprises a genus of about 60 species of herbaceous perennials many of which, or the hybrids thereof, are suitable for cultivar in the home or greenhouse. *Phalaenopsis* is predominantly epiphytic or rock dwelling, and is native to tropical Asia, the Malay Archipelago, and Oceania. The species typically has 2-ranked, fleshy, oblong or elliptic leaves affixed to a short central stem (monopodial growth), which vary in size from 12 to 20 cm to over 60 cm. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petals, called the labellum, are threelobed and are often more brightly-colored than the other flower segments. Flower colors include various shades of pink, white, yellow, and red-brown.

*Phalaenopsis* orchids are typically propagated from seeds. Asexual propagation of *Phalaenopsis* is often done from off-shoots which arise from the lower bracts of the inflorescence. The resulting plants are detached from the mother plants and may be planted in a suitable substrate.

The new *Phalaenopsis* 'PHALCRYO' is particularly characterized by its attractive and unique small, light-purple striped flowers with a light red-purple lip, economical propagation by tissue culture, rapid growth, and a plant dimension suitable for packaging and shipping to the market.

'PHALCRYO' is a product of a planned breeding program conducted by the inventor in Bleiswijk, The Netherlands.

The new *Phalaenopsis* 'PHALCRYO' originated from a cross made in December 2001 in Bleiswijk, The Netherlands. The female parent is a *Phalaenopsis* pot plant named '00001-1104' (unpatented) with white flowers with a center pattern, while the male parent is a *Phalaenopsis* pot plant named '00001-0269' (unpatented) with light purple flowers. A single plant was selected in December 2005 and has been asexually reproduced repeatedly by meristem tissue culture in Bleiswijk, The Netherlands over a 6.5-year period. The new variety has been found to retain its distinctive characteristics through successive asexual propagations.

Asexual reproduction of 'PHALCRYO' by tissue culture was first performed in February 2009 in Bleiswijk, The Netherlands and has demonstrated that the new cultivar is firmly fixed and retained through successive generations of asexual reproduction.

Plant Breeder's Rights for this variety have not been applied for. 'PHALCRYO' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands.

1) Small, light-purple striped flowers with a light red-purple lip;
2) 1 to 3 peduncles;
3) Inflorescence is short and moderate;
4) Shape of the leaf is oblong; and
5) Plants are propagated by meristem tissue culture.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs are of a 50-week old plant grown in a greenhouse in Bleiswijk, The Netherlands in August 2015.

DESCRIPTION OF THE NEW VARIETY

Figure 1:
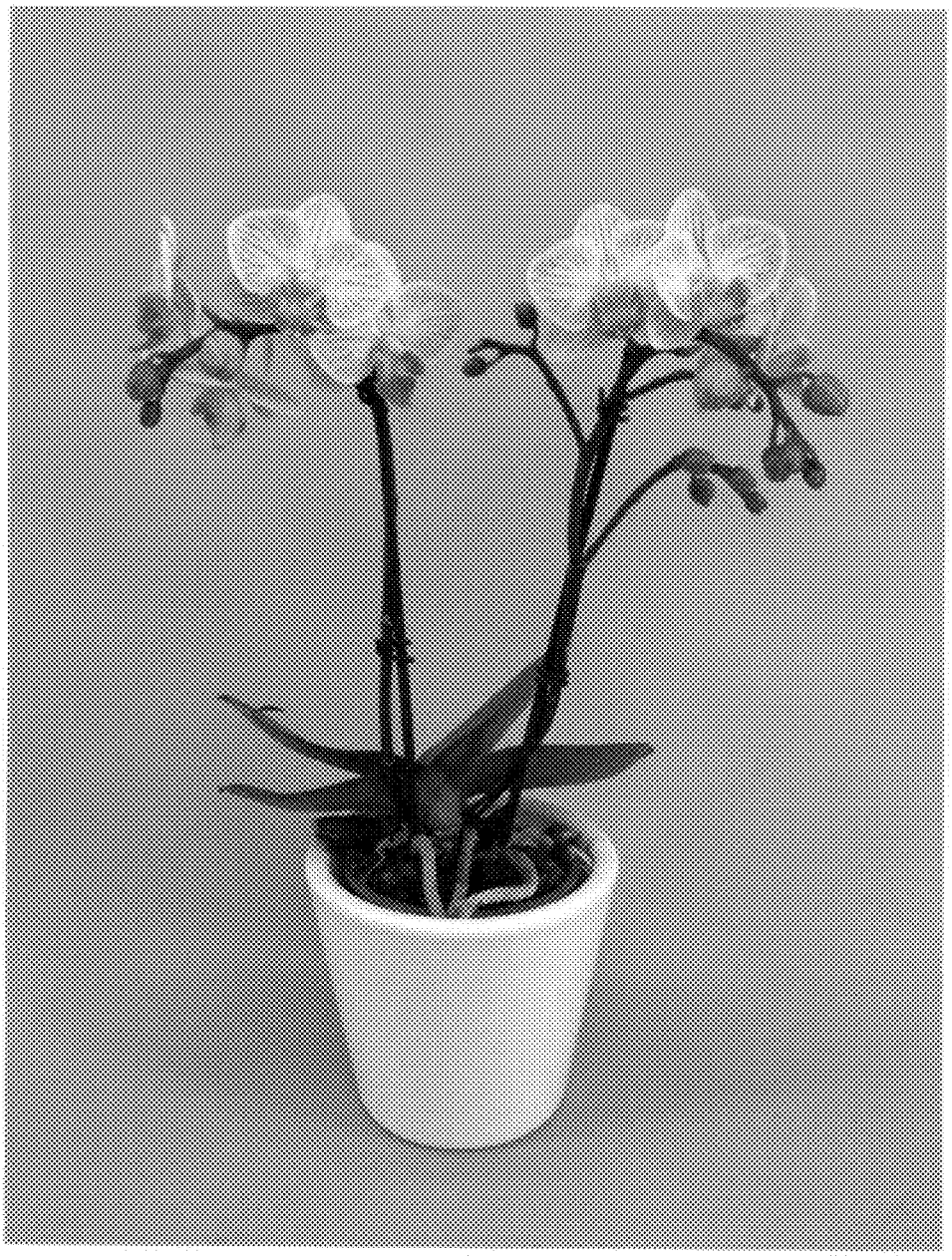
FIG. 1 shows the overall plant habit, including blooms, buds and foliage of 'PHALCRYO'.
Figure 2:
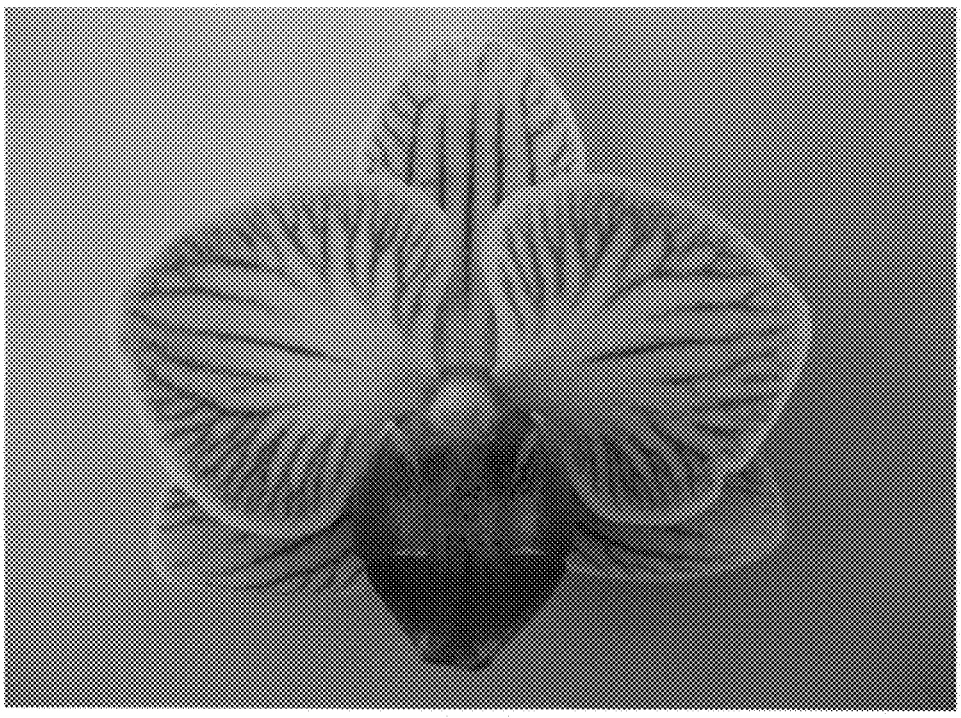
FIG. 2 shows a close-up of a flower of 'PHALCRYO'.
Figure 3:
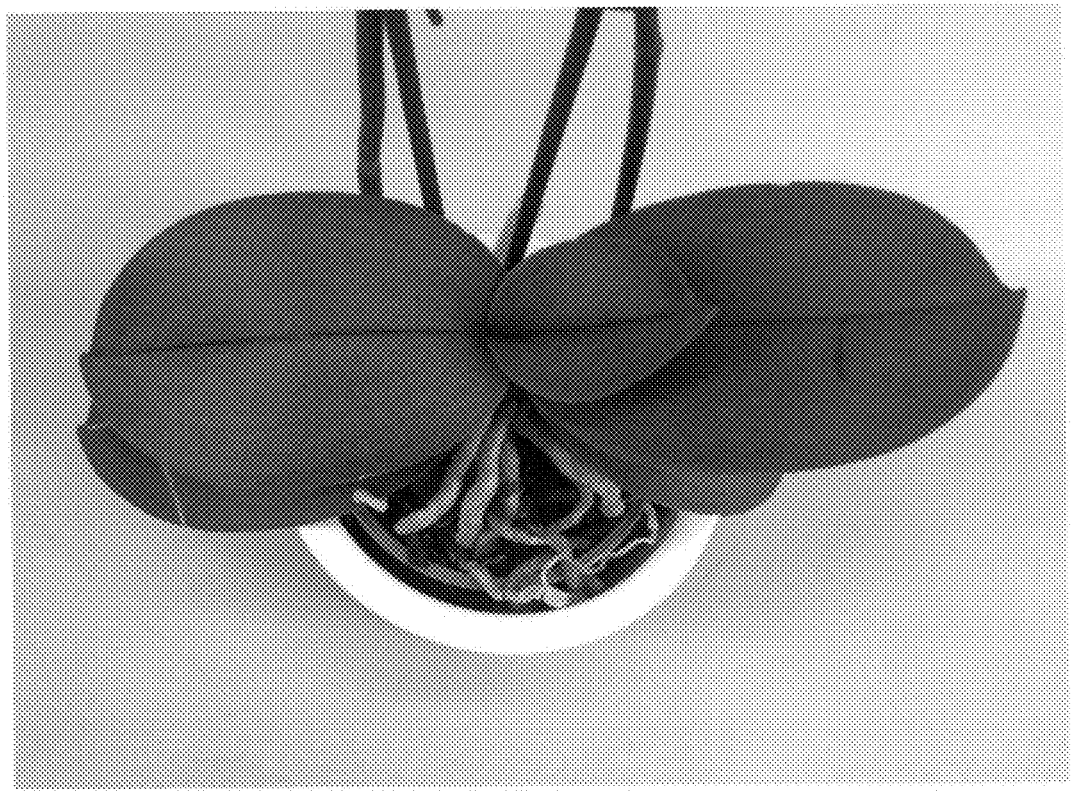
FIG. 3 shows a close-up of the leaves of 'PHALCRYO'.

The following detailed description sets forth the distinctive characteristics of 'PHALCRYO'. The data which define these characteristics were collected from asexual reproductions carried out in Bleiswijk, The Netherlands. The plant history was taken on 40-week old plants which were planted from a nursery tray in 9 centimeter pots and grown in a greenhouse between 27° C. to 29° C. for 30 weeks, continued by a cooling period of 8 weeks between 18° C. to 20° C. and 12 weeks in a greenhouse of 21° C. Observations were made in August 2015. Color readings were taken under 4-6000 lux natural light in the greenhouse. Color references are primarily to The R.H.S. Colour Chart of The Royal Horticultural Society of London (R.H.S.) (1995).

DETAILED BOTANICAL DESCRIPTION

Classification:

*Family*.—Orchidaceae.

*Botanical*.—*Phalaenopsis* hybrid.

*Common name*.—*Phalaenopsis*.

*Variety name*.—'PHALCRYO'.

Parentage:

*Female parent*.—*Phalaenopsis* cultivar '00001-1104' (unpatented).

*Male parent*.—*Phalaenopsis* cultivar '00001-0269' (unpatented).

Propagation:

*Type*.—Meristem tissue culture.

Plant:

*Crop time* (*time to produce a finished flowering plant*).—38 to 40 weeks for a 9 cm pot.

*Growth habit of inflorescence*.—Standard, green leaves, panicle.

*Height* (*including pot, including inflorescence*).—32.0 cm to 42.0 cm.

*Width* (*measured from leaf tips*).—19.0 cm to 21.0 cm.

*Vigor*.—Moderate.

Roots:

*Root description*.—Greyed-green colored roots with light branching lateral roots having light green-colored root tips.

Leaves:

*Mature leaves*.—Quantity per plant: 7 to 9 leaves are produced before flowering. Length (fully expanded): 8.0 cm to 10.0 cm. Width: 6.0 cm to 7.0 cm. Shape: Oblong. Base shape: Slightly elongated. Apex: Unequal mucronate. Leaf blade angle with the petiole (measured from the horizontal position): Between 0 degrees and 45 degrees. Leaf margin: Entire. Color: Upper surface: mix of RHS 147A and 147B with edge RHS 187A. Lower surface: RHS 147B and diluted 187A. Texture: Rough. Thickness: 2.3 mm to 2.6 mm. Venation: Pattern: Parallel. Color of the midvein: Upper surface: RHS 147A. Lower surface: mix of RHS 147A and diluted 187A.

Peduncle:

*Quantity per plant*.—1 to 3.

*Number of flowers per peduncle*.—17 to 25.

*Length*.—26.0 cm to 31.0 cm.

*Diameter*.—4.1 mm to 4.4 mm.

*Strength*.—Strong.

*Aspect*.—Upright to slightly pedant.

*Texture*.—Smooth.

*Color*.—Mix of brown (RHS 200A) and green (RHS 147A and 147B).

*Internode length*.—50.0 mm to 60.0 mm.

*Callosities*.—None.

Inflorescence description:

*Appearance*.—Upright to slightly pendant, panicle inflorescence with bilaterally symmetrical flowers that open in succession beginning with the lowermost flower.

*Inflorescence size*.—Height (from base to tip): 120.0 mm to 170.0 mm.

*Flowering time*.—First flowers can be expected 7 to 8 months after planting in a 9 cm pot.

*Flower*.—Height: 37.0 mm to 42.0 mm. Diameter: 45.0 mm to 50.0 mm. Depth of lip: 13.0 mm to 15.0 mm.

*Flower longevity*.—On the plant: 7 to 9 weeks.

*Fragrance*.—Absent.

*Flower bud*.—Average size: Small to medium. Length: 9.0 mm to 11.0 mm. Width: 12.0 mm to 14.0 mm. Shape: Egg shaped. Color: Mix of greyed-purple (RHS 184B and 70A) and light green (RHS 145B).

*Petals*.—Arrangement: Open/free. Shape: Semi-circular. Apex: Rounded/obtuse asymmetric. Margin: Entire. Length (from base to tip): 22.0 mm to 24.0 mm. Width: 25.0 mm to 27.0 mm. Color (when fully opened): Upper surface: Basic color: White (RHS 155C) striped (RHS 78B). Over color: Light purple (RHS 78C). Lower surface: Basic color: Light purple (RHS 78B) with stripes (RHS 76C and 80D) and white edge (RHS 155C). Over color: Absent.

*Dorsal sepal*.—Shape: Elliptic. Apex: Rounded symmetric. Margin: Entire. Length (from base to tip): 24.0 mm to 26.0 mm. Width: 18.0 mm to 20.0 mm. Color (when fully opened): Upper surface: Basic color: White (RHS 155C) striped (RHS 78A). Over color: Light purple at the base (RHS 78D). Lower surface: Basic color: Light purple (RHS 76D) with white edge (RHS 155C). Over color: Light purple at the base (RHS 78D).

*Lateral sepals*.—Shape: Ovate. Apex: Obtuse asymmetric. Margin: Entire. Length (from base to tip): 24.0 mm to 26.0 mm. Width: 17.0 mm to 19.0 mm. Color (when fully opened): Upper surface: Basic color: White (RHS 155C). Over color: Light green (RHS 145C) striped and dotted at the base (RHS 78B). Lower surface: Basic color: Light purple (RHS 75C) striped (RHS 78D). Over color: Light green (RHS 145C to 145D).

*Labellum* (*lip*).—Margin: Entire. Whiskers: Present. Length of whiskers: 1.0 mm to 3.0 mm. Color of whiskers: Red-purple (RHS 64A) with small yellow tips (RHS 2D) which are almost not visible. Pubescence on the lip: Absent.

*Lateral lobe*.—Shape: Type V (as described in the International Union for the Protection of New Varieties of Plants (UPOV) Test Guidelines for *Phalaenopsis*); spatulate. Length (from base to tip): 12.0 mm to 14.0 mm. Width: 9.0 mm to 11.0 mm. Color: Red-purple (RHS 59A and 64B) with yellow at the base (RHS 5A).

*Apical lobe*.—Shape: Triangular/ovate. Length (from base to tip): 11.0 mm to 13.0 mm. Width: 14.0 mm to 16.0 mm. Color: Red-purple (RHS 59A and 64A) with a touch of yellow at the base (RHS 5A).

*Callus*.—Average size: Small. Height: 0.3 cm to 0.5 cm. Length: 0.3 cm to 0.5 cm. Width: 0.3 cm to 0.4 cm. Color: Yellow (RHS 7A) dotted (RHS 185A).

Reproductive organs:

*Arrangement*.—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.

*Column*.—Length: 8.0 mm to 10.0 mm. Diameter: 4.1 mm to 4.4 mm. Color: Light purple (RHS 78D) with white top (RHS 155C).

*Pollinia*.—Quantity: 2. Size: 0.7 mm to 0.9 mm. Color: Orange (RHS 25B).

*Ovary*.—Part of the pedicel with small ribs towards the column. Length: 3.0 mm to 5.0 mm. Diameter: 1.7 mm to 1.9 mm.

*Pedicel*.—Length: 18.0 mm to 20.0 mm. Diameter: 1.9 mm to 2.1 mm. Color: Green (RHS 146C and 145C to 145D) from the inflorescence and light purple towards the flower (RHS 75C and 78D).

Disease, pest, and stress resistance: No specific resistance or susceptibility observed.

Temperature tolerance: Tolerant to a low temperature of 15° C. and a high temperature of about 30° C.

COMPARISON WITH PARENTAL AND COMMERCIAL VARIETIES

'PHALCRYO' differs from female parent plant '00001-1104' (unpatented) in that 'PHALCRYO' has striped flowers and an evenly colored leaf, whereas '00001-1104' has flowers with a center pattern and a mottled leaf. Additionally, 'PHALCRYO' has a light purple column with a white tip, whereas '00001-1104' has a white column.

'PHALCRYO' differs from male parent plant '00001-0269' (unpatented) in that 'PHALCRYO' has lighter colored flowers and a light purple column with a white tip, whereas '00001-0269' has darker colored flowers and a purple column. Additionally, the lateral sepals of 'PHALCRYO' have a light green over color, whereas the lateral sepals of '00001-0269' do not have a green over color.

'PHALCRYO' differs from commercial variety 'CHUNLI' (unpatented) in that 'PHALCRYO' has a light purple column with a white tip and a flower without a center, whereas 'CHUNLI' has a darker colored column and a flower with a center. Additionally, 'PHALCRYO' has a lighter colored flower than 'CHUNLI'.

I claim:

1. A new and distinct variety of *Phalaenopsis* plant named 'PHALCRYO', substantially as described and illustrated herein.

* * * * *